United States Patent
Boonen et al.

(10) Patent No.: US 10,039,826 B2
(45) Date of Patent: Aug. 7, 2018

(54) PHARMACEUTICAL FORMULATION COMPRISING ANTIBODIES WHICH BIND COLONY STIMULATING FACTOR-1 RECEPTOR (CSF1R)

(71) Applicant: UCB Biopharma SPRL, Brussels (BE)

(72) Inventors: Michael Joseph Edouard Boonen, Brussels (BE); Claude Peerboom, Brussels (BE)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/549,528

(22) PCT Filed: Feb. 5, 2016

(86) PCT No.: PCT/EP2016/052494
§ 371 (c)(1),
(2) Date: Aug. 8, 2017

(87) PCT Pub. No.: WO2016/128318
PCT Pub. Date: Aug. 18, 2016

(65) Prior Publication Data
US 2018/0028652 A1    Feb. 1, 2018

(30) Foreign Application Priority Data
Feb. 9, 2015 (EP) .................................... 15154301

(51) Int. Cl.
*A61K 39/395* (2006.01)
*C07K 16/28* (2006.01)
*A61K 47/18* (2017.01)
*A61K 47/26* (2006.01)
*A61K 47/12* (2006.01)

(52) U.S. Cl.
CPC ........ *A61K 39/39591* (2013.01); *A61K 47/12* (2013.01); *A61K 47/183* (2013.01); *A61K 47/26* (2013.01); *C07K 16/2866* (2013.01); *C07K 2317/21* (2013.01); *C07K 2317/24* (2013.01); *C07K 2317/56* (2013.01); *C07K 2317/565* (2013.01); *C07K 2317/76* (2013.01)

(58) Field of Classification Search
CPC .. A61K 39/39591; A61K 47/12; A61K 47/26; A61K 47/183; C07K 16/2866; C07K 2317/21; C07K 2317/24; C07K 2317/56; C07K 2317/565; C07K 2317/76
See application file for complete search history.

(56) References Cited

U.S. PATENT DOCUMENTS 8,206,715 B2 *  6/2012  Wong ................. C07K 16/2866
                                                              424/143.1
2007/0086979 A1   4/2007  Chevrier et al.

FOREIGN PATENT DOCUMENTS

WO    2013/087699    6/2013
WO    2014/036076    3/2014

* cited by examiner

*Primary Examiner* — Robert S Landsman
(74) *Attorney, Agent, or Firm* — Medler Ferro Woodhouse & Mills PLLC

(57) ABSTRACT

The current invention relates to a new pharmaceutical formulation, in particular to a pharmaceutical formulation comprising a protein, more particularly an antibody as an active ingredient.

15 Claims, No Drawings

SEQUENCE LISTING

```
<160> NUMBER OF SEQ ID NOS: 14

<210> SEQ ID NO 1
<211> LENGTH: 11
<212> TYPE: PRT
<213> ORGANISM: Artificial Sequence
<220> FEATURE:
<223> OTHER INFORMATION: CA019_969 Ab sequences CDR-L1

<400> SEQUENCE: 1

Leu Ala Ser Glu Asp Ile Tyr Asp Asn Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CA019_969 Ab sequences CDRL2

<400> SEQUENCE: 2

Tyr Ala Ser Ser Leu Gln Asp
1               5

<210> SEQ ID NO 3
<211> LENGTH: 9
<212> TYPE: PRT
<213> ORGANISM: Artificial Sequence
<220> FEATURE:
<223> OTHER INFORMATION: CA019_969 Ab sequences CDR-L3

<400> SEQUENCE: 3

Leu Gln Asp Ser Glu Tyr Pro Trp Thr
```

```
<210> SEQ ID NO 4
<211> LENGTH: 12
<212> TYPE: PRT
<213> ORGANISM: Artificial Sequence
<220> FEATURE:
<223> OTHER INFORMATION: CA019_969 Ab sequences CDR-H1

<400> SEQUENCE: 4

Gly Phe Ser Leu Thr Thr Tyr Gly Met Gly Val Gly
1               5                   10

<210> SEQ ID NO 5
<211> LENGTH: 16
<212> TYPE: PRT
<213> ORGANISM: Artificial Sequence
<220> FEATURE:
<223> OTHER INFORMATION: CA019_969 Ab sequences CDR-H2

<400> SEQUENCE: 5

Asn Ile Trp Trp Asp Asp Asp Lys Tyr Tyr Asn Pro Ser Leu Lys Asn
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: CA019_969 Ab sequences CDR-H3

<400> SEQUENCE: 6

Ile Gly Pro Ile Lys Tyr Pro Thr Ala Pro Tyr Arg Tyr Phe Asp Phe
1               5                   10                  15

<210> SEQ ID NO 7
<211> LENGTH: 107
<212> TYPE: PRT
<213> ORGANISM: Artificial Sequence
<220> FEATURE:
<223> OTHER INFORMATION: 969 gL7 V-region

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asp Asn
                20                  25                  30

Leu Ala Trp Tyr Gln Gln Lys Pro Gly Lys Ala Pro Lys Leu Leu Ile
            35                  40                  45

Tyr Tyr Ala Ser Ser Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Asp Ser Glu Tyr Pro Trp
                85                  90                  95

Thr Phe Gly Gly Gly Thr Lys Val Glu Ile Lys
            100                 105

<210> SEQ ID NO 8
<211> LENGTH: 127
<212> TYPE: PRT
<213> ORGANISM: Artificial Sequence
<220> FEATURE:
<223> OTHER INFORMATION: 969 gL7 V-region with signal sequence
``` underlined and italicized

<400> SEQUENCE: 8

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Leu Ala Ser Glu Asp
        35                  40                  45

Ile Tyr Asp Asn Leu Ala Trp Tyr Gln Gln Lys Pro Gly Lys Ala Pro
    50                  55                  60

Lys Leu Leu Ile Tyr Tyr Ala Ser Ser Leu Gln Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Leu Gln Asp Ser
            100                 105                 110

Glu Tyr Pro Trp Thr Phe Gly Gly Gly Thr Lys Val Glu Ile Lys
        115                 120                 125

<210> SEQ ID NO 9
<211> LENGTH: 214
<212> TYPE: PRT
<213> ORGANISM: Artificial Sequence
<220> FEATURE:
<223> OTHER INFORMATION: 969 gL7 light chain (V + constant)

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Tyr Asp Asn
            20                  25                  30

Leu Ala Trp Tyr Gln Gln Lys Pro Gly Lys Ala Pro Lys Leu Leu Ile
        35                  40                  45

Tyr Tyr Ala Ser Ser Leu Gln Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Leu Gln Asp Ser Glu Tyr Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 10
<211> LENGTH: 234
<212> TYPE: PRT
<213> ORGANISM: Artificial Sequence
<220> FEATURE:
<223> OTHER INFORMATION: 969 gL7 light chain (V + constant) with signal
      sequence underlined and italicized

<400> SEQUENCE: 10

Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Leu Ala Ser Glu Asp
        35                  40                  45

Ile Tyr Asp Asn Leu Ala Trp Tyr Gln Gln Lys Pro Gly Lys Ala Pro
    50                  55                  60

Lys Leu Leu Ile Tyr Tyr Ala Ser Ser Leu Gln Asp Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Tyr Cys Leu Gln Asp Ser
            100                 105                 110

Glu Tyr Pro Trp Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 11
<211> LENGTH: 125
<212> TYPE: PRT
<213> ORGANISM: Artificial Sequence
<220> FEATURE:
<223> OTHER INFORMATION: 969 gH2 V-region

<400> SEQUENCE: 11

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Met Gly Val Gly Trp Ile Arg Gln Pro Pro Gly Lys Ala Leu Glu
        35                  40                  45

Trp Leu Ala Asn Ile Trp Trp Asp Asp Asp Lys Tyr Tyr Asn Pro Ser
    50                  55                  60

```
Leu Lys Asn Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Gly Pro Ile Lys Tyr Pro Thr Ala Pro Tyr Arg Tyr
            100                 105                 110

Phe Asp Phe Trp Gly Gln Gly Thr Met Val Thr Val Ser
        115                 120                 125

<210> SEQ ID NO 12
<211> LENGTH: 144
<212> TYPE: PRT
<213> ORGANISM: Artificial Sequence
<220> FEATURE:
<223> OTHER INFORMATION: 969 gH2 V-region with signal sequence
      underlined and italicized

<400> SEQUENCE: 12

Met Glu Trp Ser Trp Val Phe Leu Phe Phe Leu Ser Val Thr Thr Gly
 1               5                  10                  15

Val His Ser Glu Val Thr Leu Lys Glu Ser Gly Pro Ala Leu Val Lys
                20                  25                  30

Pro Thr Gln Thr Leu Thr Leu Thr Cys Thr Phe Ser Gly Phe Ser Leu
            35                  40                  45

Thr Thr Tyr Gly Met Gly Val Gly Trp Ile Arg Gln Pro Pro Gly Lys
        50                  55                  60

Ala Leu Glu Trp Leu Ala Asn Ile Trp Trp Asp Asp Lys Tyr Tyr
 65                  70                  75                  80

Asn Pro Ser Leu Lys Asn Arg Leu Thr Ile Ser Lys Asp Thr Ser Lys
                 85                  90                  95

Asn Gln Val Val Leu Thr Met Thr Asn Met Asp Pro Val Asp Thr Ala
            100                 105                 110

Thr Tyr Tyr Cys Ala Arg Ile Gly Pro Ile Lys Tyr Pro Thr Ala Pro
        115                 120                 125

Tyr Arg Tyr Phe Asp Phe Trp Gly Gln Gly Thr Met Val Thr Val Ser
    130                 135                 140

<210> SEQ ID NO 13
<211> LENGTH: 453
<212> TYPE: PRT
<213> ORGANISM: Artificial Sequence
<220> FEATURE:
<223> OTHER INFORMATION: 969 gH2 heavy chain (V + constant - hu IgG4P)

<400> SEQUENCE: 13

Glu Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Thr Thr Tyr
                20                  25                  30

Gly Met Gly Val Gly Trp Ile Arg Gln Pro Pro Gly Lys Ala Leu Glu
            35                  40                  45

Trp Leu Ala Asn Ile Trp Trp Asp Asp Lys Tyr Tyr Asn Pro Ser
        50                  55                  60

Leu Lys Asn Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Gly Pro Ile Lys Tyr Pro Thr Ala Pro Tyr Arg Tyr
```

```
            100                 105                 110
Phe Asp Phe Trp Gly Gln Gly Thr Met Val Thr Val Ser Ser Ala Ser
            115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
        195                 200                 205

Cys Asn Val Asp His Lys Pro Ser Asn Thr Lys Val Asp Lys Arg Val
210                 215                 220

Glu Ser Lys Tyr Gly Pro Pro Cys Pro Pro Cys Pro Ala Pro Glu Phe
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser Gln Glu Asp Pro Glu Val Gln Phe Asn Trp Tyr Val Asp Gly Val
        275                 280                 285

Glu Val His Asn Ala Lys Thr Lys Pro Arg Glu Glu Gln Phe Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Gly Leu Pro Ser
                325                 330                 335

Ser Ile Glu Lys Thr Ile Ser Lys Ala Lys Gly Gln Pro Arg Glu Pro
            340                 345                 350

Gln Val Tyr Thr Leu Pro Pro Ser Gln Glu Glu Met Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Arg Leu
                405                 410                 415

Thr Val Asp Lys Ser Arg Trp Gln Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Leu Gly Lys
        450

<210> SEQ ID NO 14
<211> LENGTH: 472
<212> TYPE: PRT
<213> ORGANISM: Artificial Sequence
<220> FEATURE:
<223> OTHER INFORMATION: 969 gH2 heavy chain (V + constant - hu IgG4P)
      with signal sequence underlined and italicised

<400> SEQUENCE: 14
```

-continued

```
Met Glu Trp Ser Trp Val Phe Leu Phe Phe Leu Ser Val Thr Thr Gly
  1               5                  10                  15
Val His Ser Glu Val Thr Leu Lys Glu Ser Gly Pro Ala Leu Val Lys
                 20                  25                  30
Pro Thr Gln Thr Leu Thr Leu Thr Cys Thr Phe Ser Gly Phe Ser Leu
                 35                  40                  45
Thr Thr Tyr Gly Met Gly Val Gly Trp Ile Arg Gln Pro Pro Gly Lys
 50                  55                  60
Ala Leu Glu Trp Leu Ala Asn Ile Trp Trp Asp Asp Lys Tyr Tyr
 65                  70                  75                  80
Asn Pro Ser Leu Lys Asn Arg Leu Thr Ile Ser Lys Asp Thr Ser Lys
                 85                  90                  95
Asn Gln Val Val Leu Thr Met Thr Asn Met Asp Pro Val Asp Thr Ala
                100                 105                 110
Thr Tyr Tyr Cys Ala Arg Ile Gly Pro Ile Lys Tyr Pro Thr Ala Pro
                115                 120                 125
Tyr Arg Tyr Phe Asp Phe Trp Gly Gln Gly Thr Met Val Thr Val Ser
                130                 135                 140
Ser Ala Ser Thr Lys Gly Pro Ser Val Phe Pro Leu Ala Pro Cys Ser
145                 150                 155                 160
Arg Ser Thr Ser Glu Ser Thr Ala Ala Leu Gly Cys Leu Val Lys Asp
                165                 170                 175
Tyr Phe Pro Glu Pro Val Thr Val Ser Trp Asn Ser Gly Ala Leu Thr
                180                 185                 190
Ser Gly Val His Thr Phe Pro Ala Val Leu Gln Ser Ser Gly Leu Tyr
                195                 200                 205
Ser Leu Ser Ser Val Val Thr Val Pro Ser Ser Ser Leu Gly Thr Lys
                210                 215                 220
Thr Tyr Thr Cys Asn Val Asp His Lys Pro Ser Asn Thr Lys Val Asp
225                 230                 235                 240
Lys Arg Val Glu Ser Lys Tyr Gly Pro Pro Cys Pro Pro Cys Pro Ala
                245                 250                 255
Pro Glu Phe Leu Gly Gly Pro Ser Val Phe Leu Phe Pro Pro Lys Pro
                260                 265                 270
Lys Asp Thr Leu Met Ile Ser Arg Thr Pro Glu Val Thr Cys Val Val
                275                 280                 285
Val Asp Val Ser Gln Glu Asp Pro Glu Val Gln Phe Asn Trp Tyr Val
                290                 295                 300
Asp Gly Val Glu Val His Asn Ala Lys Thr Lys Pro Arg Glu Glu Gln
305                 310                 315                 320
Phe Asn Ser Thr Tyr Arg Val Val Ser Val Leu Thr Val Leu His Gln
                325                 330                 335
Asp Trp Leu Asn Gly Lys Glu Tyr Lys Cys Lys Val Ser Asn Lys Gly
                340                 345                 350
Leu Pro Ser Ser Ile Glu Lys Thr Ile Ser Lys Ala Lys Gly Gln Pro
                355                 360                 365
Arg Glu Pro Gln Val Tyr Thr Leu Pro Pro Ser Gln Glu Glu Met Thr
                370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asn Asn Tyr
                405                 410                 415
Lys Thr Thr Pro Pro Val Leu Asp Ser Asp Gly Ser Phe Phe Leu Tyr
```

```
                420                 425                 430
Ser Arg Leu Thr Val Asp Lys Ser Arg Trp Gln Glu Gly Asn Val Phe
            435                 440                 445

Ser Cys Ser Val Met His Glu Ala Leu His Asn His Tyr Thr Gln Lys
    450                 455                 460

Ser Leu Ser Leu Ser Leu Gly Lys
465             470
```

PHARMACEUTICAL FORMULATION COMPRISING ANTIBODIES WHICH BIND COLONY STIMULATING FACTOR-1 RECEPTOR (CSF1R)

FIELD OF THE INVENTION

The present invention belongs to the field of pharmaceutical formulations. More specifically, it relates to a pharmaceutical formulation comprising a protein such as an antibody.

BACKGROUND OF THE INVENTION

Antibodies, as other protein therapeutics are large and complex molecules and are inherently instable when stored over a period of time, both chemically and physically, potentially resulting in a reduction or loss of activity. Typical chemical instability may result in deamidation, hydrolysis, oxidation, beta-elimination or disulfide exchanges. Physical instability can result in denaturation, aggregation or precipitation.

Therefore, for storage, transport, handling and administration pharmaceutical formulations of antibodies and other proteins have to minimize any of the above phenomena. Antibodies can be formulated in freeze-dried, i.e. lyophilized, form for reconstitution in a solvent shortly before administration, or antibodies can be formulated in liquid form, such as in an aqueous solution. Freeze-dried formulations of antibodies tend to be more stable as water is either a reactant or as a solvent facilitates the transfer of reactants and is thus critical to many routes of chemical degradation that lead to protein instability (Andya, J. D., Hsu, C. C., & Shire, S. J. (2003). Mechanisms of aggregate formation and carbohydrate excipient stabilization of lyophilized humanized monoclonal antibody formulations. AAPS. PharmSci. 5, E10). However, despite the tendency to be less stable, interest has recently focused on liquid formulations of antibodies and other proteins as these are easier and more convenient for the patient and the healthcare professional to handle and administer in comparison to freeze-dried formulations. Liquid formulations do not need to be reconstituted and can be administered with minimal preparation. However, the stabilization of proteins in liquid formulations to avoid or minimize unwanted reactions such as aggregation, precipitation or degradation remains a particular challenge. Aggregation is a particular problem. Individual protein molecules stick physically together resulting, for example, in the formation of insoluble matter or precipitate, which may no longer be active and even cause undesired immunological reactions upon administration. Additionally, a major problem caused by the aggregate formation is that during administration the pharmaceutical formulation may block syringes or pumps.

The suggested physical pathways of degradation to aggregate and particle formation are often described as resulting from a combination of conformational and colloidal stability effects. The conformational stability is the free energy difference between the native folded state and unfolded state under physiological conditions, and as such measures the propensity of an antibody to unfold. Unfolding is often responsible for the overall aggregation rate. Colloidal stability refers to the self-repulsion propensity of native state molecules mainly due to non-specific charges located at the surface area of the molecule.

Aggregation and protein degradation during long term storage are generally assessed by determining the levels of high molecular weight species (HMWS) present in the formulation after a given storage period, typically using size-exclusion chromatography (SEC). Sometimes these events can result in precipitation that is visible to the observer.

In order to be useful liquid pharmaceutical formulations of antibodies and other protein therapeutics need to be long-term stable, and minimize the above reactions in order to contain the correct amount of pharmaceutical ingredient in active form.

Consequently various stabilizers have been explored in the art to help decrease the degradation rates of antibodies via a preferred exclusion mechanism, leading to a layer of excess water surrounding the antibody, and forcing the protein to acquire a more compact state to minimize its surface area. Stabilizers include certain sugars, polyols, amino acids, salts and polymers such as polyethylene glycol. Generally a preferred stabilizer is chosen for a given formulation, although occasionally a combination of stabilizers may be used.

Typically amino acid stabilizers have been employed in liquid antibody formulations for injection, as an alternative to sugars, and generally formulated at a lower pH to optimize antibody stability. Furthermore, glycine is a frequent choice of bulking agent in freeze-dried products where crystallizable compounds are necessary, to act by providing the appropriate texture so as to avoid apparent volume and consistency issues with the formulation such as collapse during the primary drying process. A crystalline bulking agent would act as a filler increasing the density of the solid product and avoiding any risk of structure loss. A crystalline bulking agent also provides homogeneous, dense compositions, it is easy to reconstitute and has a high eutectic temperature allowing for high sublimation temperature during primary drying of the lyophilization process. In this context glycine is used due to its crystallizing, i.e. cryoprotectant, properties, however, once crystallized it no longer has stabilizing capacities, and therefore generally a further stabilizing agent is added to such a formulation.

The choice of stabilizer is also impacted by their respective risk profiles, such as possible effects on blood glucose and their effect on renal function. In this respect, sucrose when administered via an intravenous injection cannot be hydrolyzed and therefore does not affect blood glucose levels. However intravenous antibody products have been associated with renal dysfunction, acute renal failure and osmotic nephrosis, where sugar-stabilized formulations and particularly sucrose, pose the highest risk for acute renal failure due to osmotic nephrosis. Sucrose is a disaccharide comprised of the monosaccharides glucose and fructose, and compared with other organic osmolytes, sucrose is an intermediate-strength protein stabilizer (Street T. O. et al., A molecular mechanism for osmolyte-induced protein stability. Proc. Natl. Acad. Sci. USA, 2006; 103(38):13997-14002).

Additionally formulations usually contain further excipients such as buffering agents, surfactants, or bulking agents (typically present in freeze-dried formulations).

U.S. Pat. No. 8,632,778 discloses a liquid formulation containing a humanized PM-1 antibody in a histidine buffer, containing glycine and being free of sugar.

US 2004/0033228 discloses a liquid formulation comprising an antibody, mannitol, and polysorbate in a citrate or phosphate buffer.

U.S. Pat. No. 6,372,716 discloses a freeze-dried formulation containing factor IX in a histidine buffer containing glycine and sucrose.

Although antibodies have a similar overall structure, they differ in amino acid composition and their glycosylation pattern, as well as possible post-translational modifications such as charge and glycosylation variants. These differences can result in altered interactions with other components that will affect the long term stability of the resulting formulation, which will consequently also require optimization.

With the tendency towards increasing protein concentration within the formulations, to allow for lower administration volumes, the problems regarding protein aggregation and precipitation become more apparent. Given the above, there remains a need in the art to provide further improved liquid pharmaceutical formulations of antibodies with reduced protein aggregation and precipitation after long-term storage.

DETAILED DESCRIPTION OF THE INVENTION

The present invention addresses the above-identified need by providing a novel liquid formulation comprising a therapeutic protein as active ingredient, particularly an antibody. A differential stabilizing effect has now been surprisingly observed between stabilizers with respect to the appearance of soluble aggregates as compared to large insoluble aggregates (precipitates) in a liquid pharmaceutical formulation. This surprising finding has led to a new pharmaceutical formulation exhibiting reduced protein aggregation and precipitation after long term storage. In a more specific manner the invention further provides a liquid formulation comprising an antibody binding specifically to CSF1R as an active ingredient.

In a first embodiment the invention provides a liquid pharmaceutical formulation comprising an antibody as an active ingredient, glycine and sucrose.

In a second embodiment the liquid pharmaceutical formulation according to the first embodiment of the invention comprises glycine at a concentration of 20 mM to 200 mM. In another embodiment of the liquid pharmaceutical formulation of the invention, the glycine concentration is from 50 mM to 200 mM, from 75 mM to 175 mM, preferably from 100 mM to 150 mM, or 125 mM.

In a third embodiment the liquid pharmaceutical formulation according to the first or second embodiment of the invention comprises sucrose at a concentration of 20 mM to 200 mM. In another embodiment of the liquid pharmaceutical formulation of the invention, the sucrose concentration is 50 mM to 200 mM, 75 mM to 175 mM, preferably 100 mM to 150 mM, or 125 mM.

In a fourth embodiment the liquid pharmaceutical formulation according to any of the embodiments of the invention comprises at least 50 mg/ml antibody, preferably 50 mg/ml to 300 mg/ml, or 50 mg/ml to 250 mg/ml, or 50 mg/ml to 200 mg/ml, or 50 mg/ml to 150 mg/ml, or 50 mg/ml to 100 mg/ml.

In a further particular embodiment, the liquid pharmaceutical formulation according to any of the embodiments of the invention comprises 40 mg/ml to 80 mg/ml antibody, alternatively 40 mg/ml to 60 mg/ml antibody.

In a fifth embodiment the liquid pharmaceutical formulation according to any of the embodiments of the invention additionally comprises a surfactant. The skilled artisan is aware of the choice of surfactants available for use the liquid formulation according to any of the embodiments of the invention such as but not limited to polysorbate 80, polysorbate 20, lecithin, poloxamer (e.g. poloxamer 188), sodium dodecyl sulfate (SDS), sodium laurel sulfate, sodium octyl glycoside, lauryl-, myristyl-, linoleyl-, or stearyl-sulfobetaine, lauryl-, myristyl-, linoleyl- or stearyl-sarcosine, linoleyl-, myristyl-, or cetyl-betaine, lauroamidopropyl-, cocamidopropyl-, linoleamidopropyl-, myristamidopropyl-, palmidopropyl-, or isostearamidopropyl-betaine, myristamidopropyl-, palmidopropyl-, or isostearamidopropyl-dimethylamine, sodium methyl cocoyl-, or disodium methyl oleyl-taurate, polyethyl glycol, polypropyl glycol, and copolymers of ethylene and propylene glycol. In a further particular embodiment of the invention, the liquid pharmaceutical formulation comprises polysorbate 80.

In a sixth embodiment the liquid formulation of the invention comprises 0.01% to 10% Polysorbate 80. The amount of surfactant may be adjusted in accordance with the particular protein and formulation contents. Therefore in a further embodiment, the formulation of the invention comprises 0.01% to 5% Polysorbate 80, 0.01 to 1% Polysorbate 80, 0.01 to 0.1% Polysorbate 80, preferably 0.02 to 0.1%, or 0.05% Polysorbate 80.

The liquid pharmaceutical formulation according to any of the embodiments of the invention may contain a buffering agent to maintain a constant pH during storage and administration. There are many buffering agents used in the field of liquid pharmaceutical formulations, such as, but not limited to, citrate, phosphate, lactate, histidine, glutamate, maleate, tartrate, or succinate. A preferred buffer species is typically selected amongst those having a pKa that is close (+/−1 pH unit) to the preferred pH for optimal protein stability in order to maintain high buffering capacity, and is associated with the maximal demonstrated stability observed for a particular protein when placed in a series of varied buffer species. The adequate pH ranges of a formulation are generally chosen from those associated with the maximal demonstrated stability observed for a particular protein when placed in a series of varied pH formulations.

In a particular embodiment of the invention, the liquid pharmaceutical formulation according to any of the embodiments of the invention comprises citrate, preferably a citrate concentration of 10 mM to 100 mM, 10 mM to 80 mM, 10 mM to 60 mM, 25 mM to 60 mM, preferably 40 mM to 60 mM, or 50 mM.

In a further particular embodiment, the liquid pharmaceutical formulation according to any of the embodiments of the invention has a pH of 4 to 7, preferably 4 to 6, preferably 4.5 to 5.5, or 5.

In the seventh embodiment of the liquid pharmaceutical formulation according to any of the embodiments of the invention, the antibody specifically binds to colony stimulating factor-1 receptor (CSF1R).

In an eighth embodiment of the liquid pharmaceutical formulation according to any of the embodiments of the invention the specifically binds human CSF1R.

In a ninth embodiment of the liquid pharmaceutical formulation according to any of the embodiments of the invention the antibody neutralizes CSF1R.

In a tenth embodiment of the liquid pharmaceutical formulation according to any of the embodiments of the invention the antibody is a humanized or human antibody.

In a eleventh embodiment of the liquid pharmaceutical formulation according to any of the embodiments of the invention, the antibody comprises (a) a light chain comprising CDR1, CDR2 and CDR3 as defined in SEQ ID NO: 1, SEQ ID NO: 2 and SEQ ID NO: 3, respectively, and (b) a heavy chain comprising CDR1, CDR2, and CDR3 as defined in SEQ ID NO: 4, SEQ ID NO: 5 and SEQ ID NO: 6, respectively.

In a twelfth embodiment of the liquid pharmaceutical formulation according to any of the embodiments of the invention the antibody comprises a variable light chain as defined in SEQ ID NO: 7 or 8, and a variable heavy chain as defined in SEQ ID NO: 11 or 12.

In a further embodiment of the liquid pharmaceutical formulation according to any of the embodiments of the invention the antibody comprises a light chain as defined in SEQ ID NO: 9 or 10 and a heavy chain as defined in SEQ ID NO: 13 or 14.

In a thirteenth embodiment, the liquid pharmaceutical formulation of the invention comprises 40 mM to 60 mM citrate buffer at pH 5, 100 mM to 150 mM glycine, 100 mM to 150 mM sucrose and 0.02% to 0.1% polysorbate 80.

In a further particular embodiment the liquid pharmaceutical formulation according to the invention comprises at least 50 mg/ml antibody, 50 mM citrate buffer at pH 5, 125 mM glycine, 125 mM sucrose and 0.05% polysorbate 80, wherein the antibody is an anti-CSF1R antibody.

In another embodiment of the liquid pharmaceutical formulation according to any of the embodiments of the invention a stable pharmaceutical formulation exhibits an increase of equal or less than 10%, preferably equal or less than 5%, more preferably equal or less than 3.5% in high molecular weight species (HMWS) measured after three months of storage at about 35° C. Alternatively, a stable pharmaceutical formulation exhibits an increase of equal or less than 1.2%, preferably equal or less than 1.05%, in high molecular weight species (HMWS) in each case measured after 3 months of storage at about 25° C. Preferably, the amount of HMWS in the formulation is preferably measured by size exclusion chromatography.

In a further embodiment the invention provides a method for treating a mammal, particularly a human subject, comprising administering a therapeutically effective amount of the liquid pharmaceutical formulation of any of the embodiments disclosed herein comprising an antibody binding specifically to CSF1R, such as an antibody having a light chain as defined in SEQ ID NO: 9 or 10 and a heavy chain as defined in SEQ ID NO: 13 or 14, as an active ingredient to a mammal, particularly a human subject, wherein the mammal, particularly a human subject, has a disorder that may be ameliorated through treatment with such antibody binding specifically to CSF1R, whereby the disorder is cancer such as for example, leukemia and non-Hodgkin lymphoma, acute lymphoblastic leukemia, acute myeloid leukemia, adult, acute myeloid leukemia, adrenocortical carcinoma, astrocytoma, basal cell carcinoma, bile duct cancer, bladder cancer, bone cancer, such as osteosarcoma and malignant fibrous histiocytoma, glioma, ependymoma, medulloblastoma, breast cancer, bronchial adenomas, cervical cancer, chronic lymphocytic leukemia, chronic myelogenous leukemia, colon cancer, colorectal cancer, endometrial cancer, esophageal cancer, Ewing's family of tumors, extracranial germ cell tumor, extragonadal germ cell tumor, extrahepatic bile duct cancer, retinoblastoma, gallbladder cancer, gastric (stomach) cancer, gastrointestinal carcinoid tumor, gastrointestinal stromal tumor (GIST), germ cell tumor, gestational trophoblastic tumor, hairy cell leukemia, head and neck cancer, hepatocellular (liver) cancer, lymphoma, such as Hodgkin's lymphoma, Burkitt's lymphoma, cutaneous T-cell lymphoma, such as mycosis fungoides and Sezary syndrome, hypopharyngeal cancer, melanoma, such as intraocular melanoma, Kaposi's sarcoma, kidney (renal cell) cancer, laryngeal cancer, lip and oral cavity cancer, lung cancer, such as non-small cell lung cancer or small cell lung cancer, Waldenstrom's macroglobulinemia, Merkel cell carcinoma, mesothelioma, mouth cancer, multiple myeloma, myelodysplastic syndromes, nasopharyngeal cancer, neuroblastoma, oropharyngeal cancer, ovarian cancer, pancreatic cancer, parathyroid cancer, penile cancer, pharyngeal cancer, pheochromocytoma, pineoblastoma and supratentorial primitive neuroectodermal tumors, pituitary tumor, plasma cell neoplasm, pleuropulmonary blastoma, prostate cancer, rectal cancer, rhabdomyosarcoma, salivary gland cancer, sarcoma, testicular cancer, throat cancer, thymoma, thyroid cancer, urethral cancer, or Wilms' tumor.

In another further embodiment, the disorder that may be ameliorated through treatment with an antibody binding specifically to CSF1R is a fibrotic disease, such as for example pulmonary fibrosis such as idiopathic pulmonary fibrosis and cystic fibrosis, renal fibrosis, including tubular atrophy and interstitial fibrosis, liver fibrosis, liver cirrhosis, primary sclerosing cholangitis, primary biliary cirrhosis, endomyocardial fibrosis, mediastinal fibrosis, myelofibrosis, retroperitoneal fibrosis, progressive massive fibrosis, nephrogenic systemic fibrosis, Crohn's disease, keloid, myocardial infarction, scleroderma, systemic sclerosis and arthofibrosis.

The liquid pharmaceutical formulation of the invention is suitably administered to the patient at one time or over a series of treatments and may be administered to the patient at any time from diagnosis onwards; it may be administered as the sole treatment or in conjunction with other drugs or therapies useful in treating the conditions as described herein before.

The antibody molecule may be the sole active ingredient in the liquid pharmaceutical composition. Alternatively, the antibody may be administered in combination, e.g. simultaneously, sequentially or separately, with one or more other therapeutically active ingredients. Accordingly the antibody molecule in the liquid pharmaceutical composition may be accompanied by other active ingredients including other antibody ingredients, for example epidermal growth factor receptor family (EGFR, HER-2), vascular endothelial growth factor receptors (VEGFR), platelet derived growth factor receptor (PDGFR) antibodies, or non-antibody ingredients such as imatinib, dasatinib, nioltinib, basutinib, gefitinib, erlotinib, temsirolimus, vandetanib, vemurafenib, crizotinib, vorinostat, romidepsin, bortezomib, sorafenib, sunitinib, pazopanib, regorafenib, cabozantinib, Perfenidone, steroids or other drug molecules, In a specific embodiment, the liquid pharmaceutical composition of the invention comprises an antibody binding specifically to CSF1R as a first active ingredient, and additionally comprises a second active ingredient.

Active ingredient as employed herein refers to an ingredient with a pharmacological effect, such as a therapeutic effect, at a relevant dose.

The pharmaceutical compositions suitably comprise a therapeutically effective amount of antibody. The term "therapeutically effective amount" as used herein refers to an amount of a therapeutic agent needed to treat, ameliorate or prevent a targeted disease or condition, or to exhibit a detectable therapeutic, pharmacological or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount of antibody will be from 0.01 mg/kg to 500 mg/kg, for example 0.1 mg/kg to 200 mg/kg, such as 100 mg/kg.

Pharmaceutical compositions may be conveniently presented in unit dose forms containing a predetermined amount of an active agent of the invention per dose.

For the treatment of the above diseases, the appropriate dosage will vary depending upon, for example, the particular antibody to be employed, the subject treated, the mode of administration and the nature and severity of the condition being treated. In a particular embodiment the liquid pharmaceutical formulation of the invention is administered by intravenous or subcutaneous route. When administered via intravenous injection, it may be administered as a bolus injection or as a continuous infusion. The pharmaceutical formulation according to any of the embodiments of the invention may also be administered by intramuscular injection. The pharmaceutical formulation may be injected using a syringe, an injection device such as an autoinjector, a needleless device, an implant and a patch. The formulation of the invention may also be administered via inhalation using an inhalation device containing said formulation for such delivery, for example using a nebulizer or liquid inhaler.

The process for the production of antibody molecules typically comprise culturing a host cell containing a vector encoding the antibody sequence under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

An antibody or antibody fragment that can be manufactured according to industrial scales can be produced by culturing eukaryotic host cells transfected with one or more expression vectors encoding the recombinant antibody fragment. The eukaryotic host cells are preferably mammalian cells, more preferably Chinese Hamster Ovary (CHO) cells.

Mammalian cells may be cultured in any medium that will support their growth and expression of the recombinant protein, preferably the medium is a chemically defined medium that is free of animal-derived products such as animal serum and peptone. There are different cell culture mediums available to the person skilled in the art comprising different combinations of vitamins, amino acids, hormones, growth factors, ions, buffers, nucleosides, glucose or an equivalent energy source, present at appropriate concentrations to enable cell growth and protein production. Additional cell culture media components may be included in the cell culture medium at appropriate concentrations at different times during a cell culture cycle that would be known to those skilled in the art.

Mammalian cell culture can take place in any suitable container such as a shake flask or a bioreactor, which may or may not be operated in a fed-batch mode depending on the scale of production required. These bioreactors may be either stirred-tank or air-lift reactors. Various large scale bioreactors are available with a capacity of more than 1,000 L to 50,000 L, preferably between 5,000 L and 20,000 L, or to 10,000 L. Alternatively, bioreactors of a smaller scale such as between 2 L and 100 L may also be used to manufacture an antibody or antibody fragment.

An antibody or antigen-binding fragment thereof is typically found in the supernatant of a mammalian host cell culture, typically a CHO cell culture. For CHO culture processes wherein the protein of interest such as an antibody or antigen-binding fragment thereof is secreted in the supernatant, said supernatant is collected by methods known in the art, typically by centrifugation.

Therefore the antibody production method comprises a step of centrifugation and supernatant recovery after cell culture and prior to protein purification. In a further particular embodiment said centrifugation is continuous centrifugation. For avoidance of doubt, supernatant denotes the liquid lying above the sedimented cells resulting from the centrifugation of the cell culture.

Alternatively, host cells are prokaryotic cells, preferably gram-negative bacteria. More preferably, the host cells are *E. coli* cells. Prokaryotic host cells for protein expression are well known in the art (Terpe, K. (2006). Overview of bacterial expression systems for heterologous protein production: from molecular and biochemical fundamentals to commercial systems. Appl Microbiol Biotechnol 72, 211-222.). The host cells are recombinant cells which have been genetically engineered to produce the protein of interest such as an antibody fragment. The recombinant *E. coli* host cells may be derived from any suitable *E. coli* strain including from MC4100, TG1, TG2, DHB4, DH5α, DH1, BL21, K12, XL1Blue and JM109. One example is *E. coli* strain W3110 (ATCC 27,325) a commonly used host strain for recombinant protein fermentations. Antibody fragments can also be produced by culturing modified *E. coli* strains, for example metabolic mutants or protease deficient *E. coli* strains.

An antibody fragment that can be purified in accordance with the methods of the present invention is typically found in either the periplasm of the *E. coli* host cell or in the host cell culture supernatant, depending on the nature of the protein, the scale of production and the *E. coli* strain used. The methods for targeting proteins to these compartments are well known in the art (Makrides, S. C. (1996). Strategies for achieving high-level expression of genes in *Escherichia coli*. Microbiol Rev 60, 512-538.). Examples of suitable signal sequences to direct proteins to the periplasm of *E. coli* include the *E. coli* PhoA, OmpA, OmpT, LamB and OmpF signal sequences. Proteins may be targeted to the supernatant by relying on the natural secretory pathways or by the induction of limited leakage of the outer membrane to cause protein secretion examples of which are the use of the pelB leader, the protein A leader, the co-expression of bacteriocin release protein, the mitomycin-induced bacteriocin release protein along with the addition of glycine to the culture medium and the co-expression of the kil gene for membrane permeabilization. Most preferably, the recombinant protein is expressed in the periplasm of the host *E. coli*.

Expression of the recombinant protein in the *E. coli* host cells may also be under the control of an inducible system, whereby the expression of the recombinant antibody in *E. coli* is under the control of an inducible promoter. Many inducible promoters suitable for use in *E. coli* are well known in the art and depending on the promoter expression of the recombinant protein can be induced by varying factors such as temperature or the concentration of a particular substance in the growth medium. Examples of inducible promoters include the *E. coli* lac, tac, and trc promoters which are inducible with lactose or the non-hydrolyzable lactose analog, isopropyl-b-D-1-thiogalactopyranoside (IPTG) and the phoA, trp and araBAD promoters which are induced by phosphate, tryptophan and L-arabinose respectively. Expression may be induced by, for example, the addition of an inducer or a change in temperature where induction is temperature dependent. Where induction of recombinant protein expression is achieved by the addition of an inducer to the culture the inducer may be added by any suitable method depending on the fermentation system and the inducer, for example, by single or multiple shot additions or by a gradual addition of inducer through a feed. It will be appreciated that there may be a delay between the addition of the inducer and the actual induction of protein expression for example where the inducer is lactose there may be a delay before induction of protein expression occurs while any pre-existing carbon source is utilized before lactose.

*E. coli* host cell cultures (fermentations) may be cultured in any medium that will support the growth of *E. coli* and expression of the recombinant protein. The medium may be any chemically defined medium such as e.g. described in Durany O, et al. (2004). Studies on the expression of recombinant fuculose-1-phosphate aldolase in *Escherichia coli*. Process Biochem 39, 1677-1684.

Culturing of the *E. coli* host cells can take place in any suitable container such as a shake flask or a fermenter depending on the scale of production required. Various large scale fermenters are available with a capacity of more than 1,000 liters up to about 100,000 liters. Preferably, fermenters of 1,000 to 50,000 liters are used, more preferably 1,000 to 25,000, 20,000, 15,000, 12,000 or 10,000 liters. Smaller scale fermenters may also be used with a capacity of between 0.5 and 1,000 liters.

Fermentation of *E. coli* may be performed in any suitable system, for example continuous, batch or fed-batch mode depending on the protein and the yields required. Batch mode may be used with shot additions of nutrients or inducers where required. Alternatively, a fed-batch culture may be used and the cultures grown in batch mode pre-induction at the maximum specific growth rate that can be sustained using the nutrients initially present in the fermenter and one or more nutrient feed regimes used to control the growth rate until fermentation is complete. Fed-batch mode may also be used pre-induction to control the metabolism of the *E. coli* host cells and to allow higher cell densities to be reached.

If desired, the host cells may be subject to collection from the fermentation medium, e.g. host cells may be collected from the sample by centrifugation, filtration or by concentration. In this case the process typically comprises a step of centrifugation and cell recovery prior to extracting the protein.

For *E. coli* fermentation processes wherein the protein of interest such as an antibody fragment is found in the periplasmic space of the host cell it is required to release the protein from the host cell. The release may be achieved by any suitable method such as cell lysis by mechanical or pressure treatment, freeze-thaw treatment, osmotic shock, extraction agents or heat treatment. Such extraction methods for protein release are well known in the art. Therefore in a particular embodiment, the production process comprises an additional protein extraction step prior to protein purification.

The term "antibody" or "antibodies" as used herein refers to monoclonal or polyclonal antibodies. The term "antibody" or "antibodies" as used herein includes but is not limited to recombinant antibodies that are generated by recombinant technologies as known in the art. "Antibody" or "antibodies" include antibodies' of any species, in particular of mammalian species, including antibodies having two essentially complete heavy and two essentially complete light chains, human antibodies of any isotype, including $IgA_1$, $IgA_2$, IgD, $IgG_1$, $IgG_{2a}$, $IgG_{2b}$, $IgG_3$, $IgG_4$ IgE and IgM and modified variants thereof, non-human primate antibodies, e.g. from chimpanzee, baboon, rhesus or cynomolgus monkey, rodent antibodies, e.g. from mouse, rat or rabbit; goat or horse antibodies, and camelid antibodies (e.g. from camels or llamas such as Nanobodies™) and derivatives thereof, or of bird species such as chicken antibodies or of fish species such as shark antibodies. The term "antibody" or "antibodies" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e. in the framework region (FR), are additionally replaced by corresponding non-human residues. Furthermore, humanized antibodies may comprise residues that are not found in the recipient antibody or in the donor antibody. These modifications are made to further refine antibody performance. Humanization reduces the immunogenicity of non-human antibodies in humans, thus facilitating the application of antibodies to the treatment of human disease. Humanized antibodies and several different technologies to generate them are well known in the art. The term "antibody" or "antibodies" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies with specificity against a particular antigen upon immunization of the transgenic animal carrying the human germ-line immunoglobulin genes with said antigen. Technologies for producing such transgenic animals and technologies for isolating and producing the human antibodies from such transgenic animals are known in the art. Alternatively, in the transgenic animal; e.g. mouse, only the immunoglobulin genes coding for the variable regions of the mouse antibody are replaced with corresponding human variable immunoglobulin gene sequences. The mouse germline immunoglobulin genes coding for the antibody constant regions remain unchanged. In this way, the antibody effector functions in the immune system of the transgenic mouse and consequently the B cell development are essentially unchanged, which may lead to an improved antibody response upon antigenic challenge in vivo. Once the genes coding for a particular antibody of interest have been isolated from such transgenic animals the genes coding for the constant regions can be replaced with human constant region genes in order to obtain a fully human antibody. Other methods for obtaining human antibodies antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody. The term "antibody" or "antibodies" as used herein, also refers to an aglycosylated antibody.

The term "antibody" or "antibodies" as used herein not only refers to untruncated antibodies of any species, including from human (e.g. IgG) and other mammalian species, but also refers to an antibody fragment. A fragment of an antibody comprises at least one heavy or light chain immunoglobulin domain as known in the art and binds to one or more antigen(s). Examples of antibody fragments according to the invention include Fab, Fab', F(ab')$_2$, and Fv and scFv fragments; as well as diabodies, triabodies, tetrabodies, minibodies, domain antibodies (dAbs), such as sdAbs, VHH and VNAR fragments, single-chain antibodies, bispecific, trispecific, tetraspecific or multispecific antibodies formed from antibody fragments or antibodies, including but not limited to Fab-Fv or Fab-Fv-Fv constructs. Antibody fragments as defined above are known in the art.

The term "neutralizes" as used herein refers to an antibody that inhibits or substantially reduces the biological effect of the molecule to which it specifically binds. Therefore, the expression "the antibody neutralizes CSF1R" refers to an antibody that specifically binds to CSF1R and inhibits or substantially reduces the biological effect resulting from binding of this receptor to at least one of its biological ligands. One particular type of antibody that neutralizes CSF1R blocks or substantially reduces the binding of the at least one of the biological ligands to CSF1R.

The term "colony stimulating factor-1 receptor" or "CSF1R" as used herein refers to a tyrosine-protein kinase that acts as cell-surface receptor for CSF1 and interleukin 34 (IL34) and plays an essential role in the regulation of survival, proliferation and differentiation of hematopoietic precursor cells, especially mononuclear phagocytes, such as macrophages and monocytes. It promotes the release of proinflammatory chemokines in response to IL34 and CSF1, and thereby plays an important role in innate immunity and in inflammatory processes. CSF1R also plays an important role in the regulation of osteoclast proliferation and differentiation, the regulation of bone resorption, and is required for normal bone and tooth development. CSF1R is required for normal male and female fertility, and for normal development of milk ducts and acinar structures in the mammary gland during pregnancy. It also promotes reorganization of the actin cytoskeleton, regulates formation of membrane ruffles, cell adhesion and cell migration, and promotes cancer cell invasion.

CSF1 is a cytokine that controls the production, differentiation, and function of macrophages, and CSF1R mediates most if not all of the biological effects of this cytokine.

The term "Ab969.g2" as used herein means an antibody specifically binding to CSF1-R and comprises (a) a light chain comprising CDR1, CDR2 and CDR3 as defined in SEQ ID NO: 1, SEQ ID NO: 2 and SEQ ID NO: 3, respectively, and (b) a heavy chain comprising CDR1, CDR2, and CDR3 as defined in SEQ ID NO: 4, SEQ ID NO: 5 and SEQ ID NO: 6, respectively. This Ab969.g2 antibody has been previously described in PCT/EP2014/068050.

The term "specifically binds to CSF1R", "specifically binding to CSF1R", and equivalents as used herein when referring to an antibody means the antibody will bind to CSF1R with sufficient affinity and specificity to achieve a biologically meaningful effect. The antibody selected will normally have a binding affinity for CSF1R, for example, the antibody may bind CSF1R with a Kd value of between 100 nM and 1 pM. Antibody affinities may be determined by a surface plasmon resonance bases assay, such as the BIAcore assay; enzyme-linked immunoabsorbent assay (ELISA); and competition assays (e.g. RIA's), for example. Within the meaning of the present invention an antibody specifically binding to CSF1R, may also bind to another molecule; such as by way of a non-limiting example in the case of a bispecific antibody.

EXAMPLES

Example 1

Different pharmaceutical formulations of antibody Ab969.g2 at a concentration of 50 mg/mL were prepared. A number of stabilizers were screened including sucrose, trehalose, mannitol, sorbitol, glycine, sodium chloride, proline, alanine in order to investigate their effect on protein stability under storage.

Usually one stabilizer is tested per formulation but during the formulation selection effort, 21 of the 110 tested formulations included combinations of two stabilizers (e.g., glycine and sodium chloride in 7 formulations, sucrose and sodium chloride in 7 formulations, sucrose and glycine in 7 formulations). The 110 formulations were submitted to 3 month storages at 5° C., 25° C. and 35° C. in order to assess formulation stability properties.

All formulations were analyzed freshly prepared and after 1 month, 2 months and 3 months of storage at 5° C., 25° C. or 35° C. and using multiple analytical methods (visual observation, pH, concentration, dynamic light scattering, size-exclusion chromatography, charge variants, reverse-phase chromatography). At the end of the 3-months study, it appeared that the critical analytics able to discriminate between all 110 formulations were visual observation (whether visual precipitation had occurred) and the increase in levels of aggregates or high molecular weight species (HMWS) by size-exclusion chromatography (SEC). Only 13 formulations out of the 110 tested were soluble (with no visible precipitate) at all time-points in critical storage temperatures of 5° C. and 25° C. Amongst those 13 soluble formulations the one containing stabilizers 125 mM glycine and 125 mM sucrose in citrate buffer showed the lowest increase in HMWS measured by SEC.

The synergistic effect of combined sucrose and glycine in the formulation can be understood when comparing the critical analytical data obtained for the single stabilizer formulations (either 250 mM glycine or 250 mM sucrose) to those obtained for the combined stabilizer formulation.

The glycine based formulation showed precipitation after 2 months storage at 25° C. and was therefore discontinued (see Table 1), whereas the sucrose or sucrose+glycine formulations remained in solution after 3 months storage in all conditions, showing that sucrose used as a single or a combined stabilizer reduces the risk of visual precipitation.

TABLE 1

Visual appearance after 2 months storage

|  | Sucrose 250 mM | Glycine 250 mM | Sucrose 125 mM + Glycine 125 mM |
|---|---|---|---|
| 5° C. | solution | solution | solution |
| 25° C. | solution | precipitate | solution |
| 35° C. | solution | solution | solution |

Another important consideration apart from precipitation when finding an appropriate formulation, is the formation of high molecular weight species (HMWS) due to degradation and aggregation of the antibody which aren't visible to the naked eye. Presence of HMWS in the formulations is determined using size-exclusion chromatography (SEC).

Typically a level of up to 5% HMWS at the considered long term storage conditions of the drug product, is considered to comply with release and stability considerations, and is therefore acceptable.

The increase of HMWS as determined by SEC after 2 months or 3 months is provided respectively in tables 2 and 3 below, showing that glycine used as a single or a combined stabilizer reduces the increase rate of HMWS by SEC.

TABLE 2

HMWS increase determined by SEC after 2 months storage

|  | Sucrose 250 mM | Glycine 250 mM | Sucrose 125 mM + Glycine 125 mM |
|---|---|---|---|
| 25° C. | +1.17% | +0.88% | +0.88% |
| 35° C. | +2.89% | +2.43% | +2.42% |

TABLE 3

HMWS increase determined by SEC after 3 months storage

|  | Sucrose 250 mM | Glycine 250 mM | Sucrose 125 mM + Glycine 125 mM |
|---|---|---|---|
| 5° C. | +0.27% | Not Determined | +0.2% |
| 25° C. | +1.44% | Not Determined | +1.05% |
| 35° C. | +4.16% | Not Determined | +3.48% |

As may be seen from the above results, the formulation comprising a combination of sucrose and glycine shows the lowest HMWS increase, providing an approximately 35% longer expected shelf-life over the formulation comprising sucrose alone. Combined with the absence of visible precipitation over time for all tested storage conditions, this combination of stabilizers has been found surprisingly beneficial for use in liquid protein formulations, more particularly for antibody liquid formulations.

The invention claimed is:

1. A liquid pharmaceutical formulation comprising an antibody as an active ingredient, glycine and sucrose, wherein the antibody specifically binds colony stimulating factor-1 receptor (CSF1R) and wherein the antibody comprises:
   a) a light chain comprising CDR1, CDR2 and CDR3 as defined in SEQ ID NO: 1, SEQ ID NO: 2, and SEQ ID NO: 3, respectively; and
   b) a heavy chain comprising CDR1, CDR2, and CDR3 as defined in SEQ ID NO: 4, SEQ ID NO: 5 and SEQ ID NO: 6, respectively.

2. A liquid pharmaceutical formulation according to claim 1 comprising glycine at a concentration of 20 mM to 200 mM.

3. A liquid pharmaceutical formulation according to claim 1 comprising sucrose at a concentration of 20 mM to 200 mM.

4. A liquid pharmaceutical formulation according to claim 1 comprising at least 50 mg/ml antibody.

5. A liquid pharmaceutical formulation according to claim 1 comprising a surfactant.

6. A liquid pharmaceutical formulation according to claim 5 comprising 0.01% to 10% Polysorbate 80.

7. A liquid pharmaceutical formulation according to claim 1 wherein the antibody specifically binds human CSF1R.

8. A liquid pharmaceutical formulation according to claim 1 wherein the antibody neutralizes CSF1R.

9. A liquid pharmaceutical formulation according to claim 1 wherein the antibody is a humanized or human antibody.

10. A liquid pharmaceutical formulation according to claim 1 wherein the antibody comprises a variable light chain as defined in SEQ ID NO: 7 and a variable heavy chain as defined in SEQ ID NO: 11.

11. A liquid pharmaceutical formulation according to claim 1 comprising:
   40-60 mM citrate buffer at pH 5;
   100-150 mM glycine;
   100-150 mM sucrose; and
   0.02-0.1% polysorbate 80.

12. A liquid pharmaceutical formulation according to claim 11, wherein the antibody specifically binds human CSF1R.

13. A liquid pharmaceutical formulation according to claim 11 wherein the antibody neutralizes CSF1R.

14. A liquid pharmaceutical formulation according to claim 11 wherein the antibody is a humanized or human antibody.

15. A liquid pharmaceutical formulation according to claim 11 wherein the antibody comprises a variable light chain as defined in SEQ ID NO: 7 and a variable heavy chain as defined in SEQ ID NO: 11.

* * * * *